(12) United States Patent
Kyomoto et al.

(10) Patent No.: US 9,034,414 B2
(45) Date of Patent: May 19, 2015

(54) BIOMATERIAL, JOINT PROSTHESIS USING THE BIOMATERIAL AND METHOD OF PRODUCING THE SAME

(71) Applicants: KYOCERA Medical Corporation, Osaka (JP); THE UNIVERSITY OF TOKYO, Tokyo (JP); NATIONAL UNIVERSITY CORPORATION TOKYO MEDICAL AND DENTAL UNIVERSITY, Tokyo (JP)

(72) Inventors: Masayuki Kyomoto, Osaka (JP); Kazuhiko Ishihara, Tokyo (JP); Yasuhiko Iwasaki, Tokyo (JP); Toru Moro, Tokyo (JP); Kozo Nakamura, Tokyo (JP); Yoshio Takatori, Tokyo (JP); Hiroshi Kawaguchi, Tokyo (JP); Tomohiro Konno, Tokyo (JP); Noboru Yamawaki, Osaka (JP)

(73) Assignees: KYOCERA MEDICAL CORPORATION, Osaka (JP); THE UNIVERSITY OF TOKYO, Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 14/186,183
(22) Filed: Feb. 21, 2014

(65) Prior Publication Data
US 2014/0170331 A1    Jun. 19, 2014

Related U.S. Application Data

(62) Division of application No. 12/225,758, filed as application No. PCT/JP2007/056235 on Mar. 26, 2007, now Pat. No. 8,697,238.

(30) Foreign Application Priority Data

Mar. 29, 2006    (JP) .................................. 2006-091544

(51) Int. Cl.
*A61L 27/34*    (2006.01)
*B05D 3/10*    (2006.01)
(Continued)

(52) U.S. Cl.
CPC .......... *A61L 27/34* (2013.01); *Y10T 428/24917* (2015.01); *Y10T 428/24926* (2015.01);
(Continued)

(58) Field of Classification Search
CPC .......... A61L 27/34; B05D 1/18; B05D 3/067
USPC .................. 427/2.24, 2.1, 2.25, 532, 535, 407
See application file for complete search history.

(56) References Cited

U.S. PATENT DOCUMENTS
6,702,855 B1    3/2004    Steinemann et al.
7,560,023 B2    7/2009    Miyazawa et al.
(Continued)

FOREIGN PATENT DOCUMENTS
EP    1 211 268    6/2002
EP    1 225 927    7/2002
(Continued)

OTHER PUBLICATIONS
International Search Report issued Apr. 17, 2007 in International (PCT) Application No. PCT/JP2007/056235.
(Continued)

*Primary Examiner* — Cachet Sellman
(74) *Attorney, Agent, or Firm* — Wenderoth, Lind & Ponack, L.L.P.

(57) ABSTRACT

The object of the present invention is to provide a joint prosthesis, bearing material and a production method thereof, which suppresses wear in a sliding section and suppresses the production of abrasive powder even during repeated daily operation. To achieve the object, there is provided a biomaterial comprising: a substrate made of metal, alloy or ceramic; and a biocompatible material layer laminated on the substrate, wherein hydroxyl groups are formed on the substrate by surface-treating, while the biocompatible material layer comprises a polymer containing phosphorylcholine groups, the substrate and the biocompatible material layer are bound via a binder layer which is combined with the hydroxyl groups of the substrate and with the biocompatible material layer.

5 Claims, 3 Drawing Sheets

(51) Int. Cl.
  *B05D 1/36* (2006.01)
  *A61F 2/30* (2006.01)
  *A61L 27/42* (2006.01)
  *C22F 1/11* (2006.01)
  *C22F 1/18* (2006.01)
  *B05D 1/18* (2006.01)
  *B05D 3/06* (2006.01)
  *A61F 2/32* (2006.01)
  *A61F 2/34* (2006.01)
  *A61F 2/36* (2006.01)
  *B23K 35/36* (2006.01)

(52) U.S. Cl.
  CPC ............... *A61F2/30767* (2013.01); *A61F 2/32* (2013.01); *A61F 2/34* (2013.01); *A61F 2002/30685* (2013.01); *A61F 2002/30934* (2013.01); *A61F 2002/3611* (2013.01); *A61F 2310/00011* (2013.01); *A61F 2310/00179* (2013.01); *A61L 27/42* (2013.01); *B23K 35/3618* (2013.01); *C22F 1/11* (2013.01); *C22F 1/183* (2013.01); *B05D 1/18* (2013.01); *B05D 3/067* (2013.01)

(56) References Cited

U.S. PATENT DOCUMENTS 8,066,824 B2   11/2011   Breitenkamp et al.

2004/0243249 A1   12/2004   Ishihara et al.
2005/0064007 A1    3/2005   Steinemann et al.
2006/0060533 A1*   3/2006   Miyazawa et al. ............ 210/656
2007/0207321 A1*   9/2007   Abe et al. ...................... 428/413
2009/0317443 A1*  12/2009   Willis et al. ................... 424/423

FOREIGN PATENT DOCUMENTS

JP   2002-535074   10/2002
JP   2003-512895    4/2003
JP   2003-310649   11/2003
JP   2005-526541    9/2005

OTHER PUBLICATIONS

Morimoto et al., "Coating Stability and Blood Compatibility of Stainless Steel Surface Modified with Phospholipid Polymer", Kobunishi Ronbunshu, vol. 59, No. 7, 2002, pp. 432-437.

Kibayashi et al., "Surface Modification of Pure Titanium by Plasma Exposure and Its Bonding to Resin", Dental Materials Journal, vol. 24, No. 1, 2005, pp. 53-58.

Extended European Search Report issued Jun. 11, 2012 in European Application No. 077396737.

Iwasaki et al., "Immobilization of phosphorylcholine polymers to Ti-supported vinyldimethylsilyl monolayers and reduction of albumin adsorption", Colloids and Surfaces B: Biointerfaces, vol. 32, 2003, pp. 77-84.

* cited by examiner

BIOMATERIAL, JOINT PROSTHESIS USING THE BIOMATERIAL AND METHOD OF PRODUCING THE SAME

This application is a divisional application of application Ser. No. 12/225,758, filed Sep. 29, 2008, now U.S. Pat. No. 8,697,238, which is the National Stage of International Application No. PCT/JP2007/056235, filed Mar. 26, 2007, the entire disclosure of which is incorporated herein by reference.

TECHNICAL FIELD

The present invention relates to a biomaterial with hydrophilic and biocompatible characteristics, to a joint prosthesis having superior wear resistance incorporating the biomaterial and to a method of producing the biomaterial. In particular, the present invention relates to use of a bearing material used in a joint prosthesis acting as an artificial joint for a human.

BACKGROUND ART

High-strength materials such as metals or ceramics are widely used in medical fields as prosthesis covering fractured sections, such as bone prosthesis or dental prosthesis (artificial dental roots) or as prosthesis for a physical activity, such as joint prostheses. Recent developments have seen the active application of metals to artificial circulatory system. Consequently, there is a need for materials with mechanical strength as well as biocompatibility. Here the term "biocompatibility" means the property of preventing blood coagulation reactions or suitable adaptability of the inserted section to soft tissue. This sort of biocompatibility is indispensable for in vivo medical devices.

A technique is known of applying 2-methacryloyloxyethyl phosphorylcholine (hereinafter referred to as "MPC") which has superior biocompatibility as a medical polymer material. Conventionally, many biocompatible MPC polymers have been used in the form of an MPC copolymer containing hydrophobic groups resulting from the copolymerization of MPC with monomers containing hydrophobic groups. However in case that the resulting copolymer is coated onto the surface of the substrate ("surface substrate") to be used in a medical device, few problems have, if in a short timeframe, arisen by being contacted with blood. However it is quite likely for the coating to remove from the surface substrate during long-term use.

In order to avoid these problems, a technique has been disclosed in which a coating material containing a copolymer of a reactive co-monomer, such as a stryrene monomer containing amino groups or methylacrylate containing amino groups, as well as a monomer containing phosphorylcholine analogous groups has been used to fix this copolymer covalently to the substrate surface (Patent Document 1). However this technique has not generally been commercially applied due to the high price of stryrene monomers containing amino groups or methylacrylate containing amino groups.

Another method has been disclosed in which chemical bonding is used to fix an MPC copolymer containing amino groups as well as an MPC copolymer containing epoxy groups to the surface substrate in a medical device (Patent Document 2 and Patent Document 3). However difficulties have been encountered in fixing the MPC copolymer containing amino groups to the substrate surface depending on the ratio of amino group content. As a result, the coating may become fragile.

A method has been disclosed in which a random copolymer comprising allylamine and phosphorylcholine analogue groups is fixed to a medical device (Patent Document 4). For example, in case that a coated medical device is made of a metallic material, a polymer 4-methacryloxyethyltrimellitate anhydride (hereinafter referred to as "4-META") is used as a binder. The acid anhydride group contained in the 4-META polymer has superior reactivity with respect to an amino group in the random copolymer formed from allylamine and phosphorylcholine analogous groups. Consequently this binder enables a random copolymer to be fixed to the medical biomaterial.

However as described above, as the ratio of phosphorylcholine groups used in the copolymer decreases, problems have arisen that are associated with a deterioration in biocompatibility, hydrophily and surface lubricity. Furthermore a suitable solution to coating loss resulting from long-term use has yet to be found. It has been reported that after 91 days of use, only 5% of MPC copolymer remained in titanium-based artificial heart system coated with MPC copolymer (Non-Patent Document 1).

Joint prostheses such as knee joint prostheses or hip joint prostheses have been used which are generally constructed by a combination of ultrahigh molecular weight polyethylene (hereinafter referred to as "UHMWPE") and a cobalt-chromium (hereinafter referred to as "Co—Cr") alloy. However in case that joint prostheses are used in vivo, UHMWPE wear debris produced by frictional motion entered between the acetabular cup and the living bone. The wear debris are engulfed by macrophages, osteolytic cytokines are released leading to possibility of inducing osteolysis. Osteolysis leads to the serious problem that the fixing strength between the joint prosthesis and the bone is weakened, thus resulting in a complication concerning joint arthroplasty, which is termed as loosening (Non-Patent Document 2).

Normally the linear wear of the UHMWPE ranges from 0.1 mm to 0.2 mm annually and therefore no problems arise immediately after joint arthroplasty. However after approximately five years, aseptic loosening occurs as described above. It is sometimes the case that the joint prostheses should be replaced, leading to a large burden on the patient.

A method of solving the problem of loosening is to reduce the amount of UHMWPE wear debris. Therefore various tests have been performed for the purpose of improving the combination of the material used on the joint surface or improving the material itself. Especially, UHMWPE cross-linked by means of an electron beam or a radioactive-ray (cross-linked polyethylene, hereinafter referred to as "CLPE") has been actively researched in recent years.

Research is also being conducted to improve the bearing surface of UHMWPE or the like. The group led by Nobuyuki Yamamoto has produced a medical device having the biocompatibility and the surface lubricity, which is produced by fixing a random copolymer comprising allylamine and phosphorylcholine analogue groups to the surface of a medical device including a joint prosthesis (Patent Document 4). The group led by Kazuhiko Ishihara has produced a joint prosthesis in which polymer material is used which grafts polymerizable monomers containing a phosphorylcholine group onto a polymer joint prosthesis containing UHMWPE, thus suppressing the production of wear debris by reducing friction between the bearing surface of the joint prosthesis (Patent Document 5).

It has also been proposed to use a combination of hard-material members at the joint face instead of using polymer materials such as UHMWPE which can create abrasion. For example, a joint prosthesis is currently undergoing clinical uses, which is formed from a combination of a femoral head prosthesis made of a Co—Cr alloy and an acetabular cup prosthesis made of Co—Cr alloy (Non-Patent Document 3) or a combination of a femoral head prosthesis made of an alumina-ceramic and an acetabular cup prosthesis made of an alumina-ceramic (Non-Patent Document 4).

Patent Document 1: Japanese Unexamined Patent Publication (Kokai) No. 7-502053
Patent Document 2: Japanese Unexamined Patent Publication (Kokai) No. 7-184989
Patent Document 3: Japanese Unexamined Patent Publication (Kokai) No. 7-184990
Patent Document 4: International Publication No. WO 01/05855, pamphlet
Patent Document 5: Japanese Patent Unexamined Publication (Kokai) No. 2003-310649
Non-Patent Document 1: "In Vivo Evaluation of a MPC Polymer Coated Continuous Flow Left Ventricular Assist System" ARTIFICIAL ORGANS, VOL 27, NO. 2, 2003
Non-Patent Document 2: "In vivo wear of polyethylene acetabular components" THE JOURNAL OF BONE AND JOINT SURGERY, VOL 75-B, NO. 2, 1993
Non-Patent Document 3: "Engineering Issues and Wear Performance of Metal on Metal Hip Implants" CLINICAL ORTHOPEDICS AND RELATED RESEARCH, NO. 333, 1996
Non-Patent Document 4: "Wear rates of ceramic-on-ceramic bearing surfaces in total hip implants: A 12-year follow-up study" THE JOURNAL OF ALTHROPLASTY, VOL 14, NO. 7, 1999

DISCLOSURE OF INVENTION

Problems to be Solved by the Invention

However in case that a random copolymer comprising allylamine and phosphorylcholine analogue groups is applied to the surface of a medical device, the random copolymer has been sufficiently pre-polymerized not to be fixed to the surface of the medical device (corresponding to the substrate according to the present invention). Therefore, there is insufficient bonding between the random copolymer and the surface of the medical device. Consequently unsatisfactory results are obtained in case that the above prosthesis is used for a long time in vivo, and in particular, under the rigorous wear and abrasion environment of the bearing surface of a joint prosthesis. Even though it is likely for UHMWPE to be generally used as a bearing material in polymer joint prosthesis, it does not contain functional groups such as carboxyl groups, carboxylic acid anhydrides, epoxy groups, isocyanate groups to therefore have conspicuously poor binding to random copolymers comprising allylamine and phosphorylcholine analogue groups. In order to solve this problem, it has been suggested to treat the surface of the medical device by means of plasma treatment, corona treatment, ozone treatment or the like to provide carboxyl groups with the surface. However such treatments unavoidably affect the characteristics of the substrate of the medical device and unsatisfactory results are obtained. Although surface lubricity or biocompatibility can be provided by fixing a random copolymer comprising allylamine and phosphorylcholine analogue groups to the surface of the medical device, long-term wear-resistance characteristics which are the most important problem regarding bearing materials for polymer joint prostheses are not solved thereby. Furthermore in case that a coated medical device is made of a metallic material, if a 4-META polymer is used as a binder, the acid anhydride group contained in the 4-META polymer has superior reactivity by means of the random copolymer comprising allylamine and phosphorylcholine analogue groups. These random copolymers bind to the medical biomaterial via the binder. However the acid anhydride group contained in the 4-META polymer binds to the random copolymer at the same time as binding to the substrate. Thus the problem arises that if the bond to the random copolymer is strong, the bond with the substrate will become fragile. On the other hand, if the bond with the substrate is strong, the bond with the random copolymer will be fragile.

As described above, the Ishihara group graft-bonded MPC which is a polymerizable monomer comprising phosphorylcholine groups to UHMWPE which is a polymer material for joint prostheses by irradiating for 30 minutes using ultraviolet (UV) radiation at a wavelength of 300 to 400 nm. The frictional coefficient was considerably reduced as a result of the improvement in wettability. Furthermore superior abrasion characteristics were shown by a study examining sliding over 3 million cycles using a hip joint simulator. However according to hemi-arthroplasty with no acetabular cups replaced, a UHMWPE component is not used and therefore no effect is obtained. In particular, there remain concerns regarding durability in case of knee joint prostheses placed under a high surface contact-pressure condition.

Wear debris produced by friction between Co—Cr alloy components is highly cytotoxic and therefore there are safety concerns in case of use for a long term. Alumina-ceramic material used in combinations of alumina-ceramic femoral head prostheses and alumina-ceramic acetabular cup prostheses as described above is a brittle material to be sometimes broken down during surgical procedures or during in vivo use. Consequently there is a need for further improvement in order to put the same into practical use. These hard materials have poor elasticity and no cushioning function in contrast with for example, UHMWPE. Therefore these materials are not preferred since there is no damping action with respect to external forces and loads are directly applied to the bone.

The present invention is proposed to solve the above problems and the object of the present invention is to provide a biomaterial which suppresses wear in a bearing surface and suppresses the production of wear debris even during repeated daily operation. In particular, another object of the present invention is to provide a joint prosthesis, a joint prosthesis bearing material and a method of producing the same. Furthermore, yet another object of the present invention is to provide a biomaterial which has superior characteristics by retaining mechanical characteristics in vivo, allowing safe bodily use and long-term reliability and which greatly reduces the burden on a patient.

Means for Solving the Problems

The present inventors have performed diligent research in the light of the above problems and have made the surprising discovery that although biocompatible materials such as MPC do not normally strongly bind to metal, alloy or ceramic surfaces, it is possible to obtain a strong lamination of a biocompatible material layer on the metal or the like if the metal, alloy or ceramic surface is suitably treated, and the biocompatible material layer is connected to the treated metal, alloy or ceramic surface via a binding layer comprising for example, 4-META monomer.

Accordingly, in one aspect of the present invention, there is provided a biomaterial comprising:

a substrate made of at least one selected from the group consisting of metal, alloy and ceramic; and a biocompatible material layer laminated on appropriate sections of the substrate, wherein hydroxyl groups are formed on a surface of the substrate by surface-treating at least one section of the surface, while the biocompatible material layer comprises a polymer containing phosphorylcholine groups, the substrate and the biocompatible material layer are bound via a binder layer, the binder layer being combined, on the one hand, with the hydroxyl groups of the substrate and, on the other hand, with the biocompatible material layer respectively.

This biomaterial includes a biomaterial in which, for example, hydroxyl groups formed on a Co—Cr alloy surface bind with carboxyl groups formed in a 4-META monomer, while methacrylic groups in the 4-META monomer react with methacrylic groups in the MPC monomer to form copolymer.

Examples of a polymer containing phosphorylcholine groups include for example, MPC polymer or a copolymer containing MPC (for example, MPC-butylmethacrylate copolymer). On the other hand, the substrate made of metal, alloy or ceramic may contain a metal oxide or metal component capable of forming hydroxyl groups. The metal oxide or metal component as mentioned above includes titanium metals, or at least one alloy selected from the group consisting of Co—Cr alloy, cobalt-chromium-molybdenum (hereinafter referred to as "Co—Cr—Mo") alloy, nickel-chromium (hereinafter referred to as "Ni—Cr") alloy, stainless steel (hereinafter referred to as "SUS") alloy and titanium (hereinafter referred to as "Ti") alloy, or a ceramic containing at least one substance selected from the group consisting of alumina, zirconia and titania.

The above binder contains an organic compound having carboxyl groups on one terminal and methylene groups on the other terminal. The above organic compound includes for example, 4-META, 4-methacryloyloxy ethyl trimellitic acid (hereinafter referred to as "4-MET") or methacrylic acid, maleic anhydride or maleic acid.

In the other aspect of the present invention, there is provided a method for producing a biomaterial in which a biocompatible material layer is laminated at appropriate positions on a substrate made of an alloy or a ceramic material, comprising the steps of:

(a) plasma-processing a substrate made of a metal, alloy or ceramic material containing a metal component or a metal oxide capable of forming hydroxyl groups to form hydroxyl groups on the surface of the substrate;

(b) applying a solution containing a binder constituent to the substrate and then drying the solution to form a binder layer thereon, the binder constituent be an organic compound having carboxyl groups on one terminal and methacrylic groups or methylene groups on the other terminal; and (c) immersing the substrate in a solution containing a biocompatible material and a photo-initiator and then polymerizing the biocompatible material monomer on the binder layer by UV irradiation to graft-coat the biocompatible material layer on the binder layer.

In accordance with the present invention, in order to form an MPC graft coating layer, a binder monomer is pre-coated on the substrate and the double bond of the binder monomer is cleaved so that there are produced radicals each of which is used as a nucleus for the graft-polymerization of the MPC monomer. Ionic and covalent bonds exist via the binder between the MPC polymer and the metal substrate and therefore produce a strong coating. In addition, in order to form an MPC graft coating layer, a binder monomer or polymer is applied to the substrate and the C—H bond of the binder monomer or polymer is cleaved by a photo-induced polymerization method, thus producing a radical used as a nucleus for the graft-polymerization of the MPC monomer. Ionic and covalent bonds exist via the binder between the MPC polymer and the metal substrate and therefore produce a strong coating.

The production method of the present invention creates a strong bond between the MPC polymer layer and the substrate and therefore has stable characteristics as a bearing material for a joint prosthesis under the high load conditions. Therefore, according to the present invention, a biomaterial containing a metal, alloy or ceramic is coated with a biocompatible material such as MPC. Consequently even during long-term use in vivo, the material has superior hydrophilicity and biocompatibility. In particular, since the femoral head prostheses, acetabular cup prostheses made of metal or ceramic are coated with a biocompatible material such as MPC, there is no possibility of wear debris being produced and there is no effect on the human body. Furthermore combinations of Co—Cr alloy femoral heads and Co—Cr alloy acetabular cups or combinations of alumina-ceramic femoral heads and alumina-ceramic acetabular cups do not produce UHMWPE wear debris and therefore there is no possibility of occurring osteolysis.

DETAILED DESCRIPTION OF THE INVENTION

The biomaterial according to the present invention will be described in more detail, particularly with reference to a joint prosthesis, making reference to the figures. The embodiments below are merely exemplary and the present invention is not limited to the embodiments.

Embodiment 1

Figure 1:
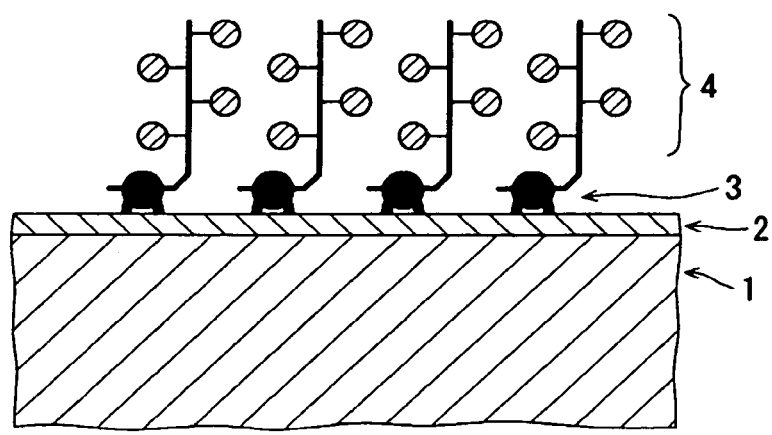
FIG. 1 is a schematic view of a biomaterial according to the present invention.

FIG. 1 shows a biomaterial according to a first embodiment of the invention. As shown in FIG. 1, the biomaterial according to the first embodiment of the invention comprises a substrate 1 made of metal, alloy or ceramic, a surface processed layer 2 which is formed on the main surface of the substrate 1 by processing at least one section of the main surface of the substrate 1, a binder layer 3 laminated on the surface processed layer 2, and a biocompatibility layer 4 laminated on the binder layer 3.

Binder Layer

The binder layer is preferably made of a substance having carboxyl groups on one terminal and methacrylic groups or methylene groups on the other terminal. This type of substance includes for example, 4-META, 4-MET, or methacrylic acid, maleic anhydride or maleic acid.

The methacrylic groups or methylene groups on one terminal are joined to methacrylic groups of the MPC of the biocompatible material. The carboxyl groups on the other terminal are connected with the hydroxyl groups which are formed on the surface of the substrate by processing it with an oxidization treatment and plasma treatment. This is because the functional group of the 4-META reacts with the oxidized coating of the surface of the alloy substrate to form metallic salts of 4-META. In case of such as Ni—Cr alloys, Co—Cr alloys, stainless, titanium or the like, oxidized coating is naturally formed on the surface thereof after an alumina sandblast treatment and therefore obtain a stronger bonding strength. 4-META shows strong adhesion to chrome hydroxides formed from chromium oxides in such as Ni—Cr or Co—Cr alloys.

Biocompatible Material Layer

The biocompatible material layer has the same chemical structure as a cell-membrane constituting biological tissue. As a result, even in the event that wear debris enters the body, the material does not cause a reaction with the internal bodily tissue and thus has no adverse effect on the body. Normally when foreign biological materials such as microorganisms, for example, bacteria or viruses enter a human organism or an organ is transplanted from another person into it, antigen groups on the surface of such foreign material are recognized by antibody molecules or immune cells in the body and provoke a bodily defense reaction, in other words, a rejection reaction. Recognition by the complement system also plays a role in biological reactions to these types of biological foreign materials. The complement system comprises approximately 20 types of blood plasma proteins and is strongly interconnected with other immune system proteins or cells. The complement system has the object of notifying immune system cells of the presence of a foreign material and killing invading microorganisms. The recognition of foreign material results in activation of complement. Consequently the introduction of materials such as bone prosthesis activates complement. When these types of materials are inserted directly into bone, the materials come into contact with biological fluids or the like and protein attaches to the surface of the material. Thus neutrophils and macrophages (phagocytes) are activated and information transmission substances termed cytokines are released. In the interface between metal and bone, for example, the metal is recognized as a foreign material as a result of metal ions given off by the material or wear debris and this causes a capsulation process in which connective tissue (soft tissue) covers the material, the formation of a non-crystal phase termed an amorphous phase or induces osteolysis due to the abrasive powder.

The biocompatible material has the same function as an in vivo biomaterial since it does not produce capsulation, protein attachment or thrombotic formation as referred to above. In particular, when disposed on the contact surface of the acetabular cup and/or the femoral head of a joint prosthesis, it is possible to prevent wear of the living bone. Furthermore abrasive powder from the biocompatible material produced as a result of sliding of the femoral head and the acetabular cup does not tend to produce a reaction with biological substances in the body and as a result, does not tend to result in osteolysis.

The biocompatible material includes polymer materials having phosphorylcholine groups. The polymer materials preferably include 2-methacryloyloxyethyl phosphorylcholine, 2-acryloyloxyethyl phosphorylcholine, 4-methacryloylbutyl phosphorylcholine, 6-methacryloyloxyhexyl phosphorylcholine, ω-methacryloyloxyethylene phosphorylcholine and 4-styryloxybutyl phosphorylcholine.

Other examples of a biocompatible material include for example 2-methacryloyloxyethyl-2'-(trimethylammonio) ethyl phosphate, 3-methacryloyloxypropyl-2'-(trimethylammonio) ethyl phosphate, 4-methacryloyloxybutyl-2'-(trimethylammonio) ethyl phosphate, 5-methacryloyloxypentyl-2'-(trimethylammonio) ethyl phosphate, 6-methacryloyloxyhexyl-2'-(trimethylammonio) ethyl phosphate, 2-methacryloyloxyethyl-2'-(triethylammonio) ethyl phosphate, 2-methacryloyloxyethyl-2'-(tripropylammonio) ethyl phosphate, 2-methacryloyloxyethyl-2'-(tributylammonio) ethyl phosphate, 2-methacryloyloxypropyl-2'-(trimethylammonio) ethyl phosphate, 2-methacryloyloxybutyl-2'-(trimethylammonio) ethyl phosphate, 2-methacryloyloxypentyl-2'-(trimethylammonio) ethyl phosphate, 2-methacryloyloxyhexyl-2'-(trimethylammonio) ethyl phosphate, 2-methacryloyloxyethyl-3'-(trimethylammonio) propyl phosphate, 3-methacryloyloxypropyl-3'-(trimethylammonio) propyl phosphate, 4-methacryloyloxybutyl-3'-(trimethylammonio) propyl phosphate, 5-methacryloyloxypentyl-3'-(trimethylammonio) propyl phosphate, 6-methacryloyloxyhexyl-3'-(trimethylammonio) propyl phosphate, 2-methacryloyloxyethyl-4'-(trimethylammonio) butyl phosphate, 3-methacryloyloxypropyl-4'-(trimethylammonio) butyl phosphate, 4-methacryloyloxybutyl-4'-(trimethylammonio) butyl phosphate, 5-methacryloyloxypentyl-4'-(trimethylammonio) butyl phosphate, and 6-methacryloyloxyhexyl-4'-(trimethylammonio) butyl phosphate.

Substrate

Metals constituting the substrate include titanium (Ti) and chromium (Cr), which have property to easily form hydroxyl groups. Alloys constituting the substrate include SUS alloys, Cr alloys and titanium alloys. Preferred examples of Cr alloys include Co—Cr alloys or Co—Cr—Mo alloys. Preferred examples of titanium alloys include Ti-6Al-4V alloy, Ti-15Mo-5Zr-3Al alloy, Ti-6Al-7Nb alloy, Ti-6Al-2Nb-1Ta alloy, Ti-15Zr-4Nb-4Ta alloy, Ti-15Mo-5Zr-3Al alloy, Ti-13Nb-13Zr alloy, Ti-12Mo-6Zr-2Fe alloy, Ti-15Mo alloy and Ti-6Al-2Nb-1Ta-0.8Mo alloy. Ceramics constituting the substrate include alumina, zirconia and titania, which are metal oxides capable of forming hydroxyl groups. These materials form oxides on the surface with plasma treatment and facilitate formation of hydroxyl groups. Thus these materials are preferably employed since the substrate and the binder layer are strongly bound by chemical bonds between their hydroxyl groups and the carboxyl groups of the binder layer. However any material may be employed as the substrate, as long as it has the property to form functional groups which can react with carboxyl groups of the binder layer formed on the substrate. The functional groups which can react with carboxyl group of the binder layer formed on the substrate are preferably hydroxyl groups. However they are not limited to the hydroxyl groups.

Production Method

Hereafter a method of producing the biomaterial according to a first embodiment of the present invention will be outlined.

Firstly the substrate made of a metal, alloy, semiconductor or ceramic was subjected to ultrasonic cleaning in an acetone solution.

Then the substrate is spin-coated with a 4-META/acetone solution. For example, ethanol can be used as the organic solvent. The concentration of the 4-META/acetone solution is preferably 2% to 20% by weight, more preferably 5% to 10% by weight, and most preferably approximately 10% by weight.

After the substrate is spin-coated as described above, it is dried under normal pressure. The temperature is preferably between 20° C. to 60° C. and more preferably approximately 40° C. The drying time is between 1 hour to 12 hours and more preferably approximately 3 hours.

The substrate is immersed in a solution in which a biocompatible material monomer and a photo-initiator are dissolved in the solvent. It is preferred that the biocompatible material monomer is made of at least one selected from the group comprising 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, ω-methacryloyloxyethylene phosphorylcholine and 4-styryloxybutyl phosphorylcholine, 2-methacryloyloxyethyl-2'-(trimethylammonio) ethyl phosphate, 3-methacryloyloxypropyl-2'-(trimethylammonio) ethyl phosphate, 4-methacryloyloxybutyl-2'-(trimethylammonio) ethyl phosphate, 5-methacryloyloxypentyl-2'-(trimethylammonio) ethyl phosphate, 6-methacryloyloxyhexyl-2'-(trimethylammonio) ethyl phosphate, 2-methacryloyloxyethyl-2'-(triethylammonio) ethyl phosphate, 2-methacryloyloxyethyl-2'-(tripropylammonio) ethyl phosphate, 2-methacryloyloxyethyl-2'-(tributylammonio) ethyl phosphate, 2-methacryloyloxypropyl-2'-(trimethylammonio) ethyl phosphate, 2-methacryloyloxybutyl-2'-(trimethylammonio) ethyl phosphate, 2-methacryloyloxypentyl-2'-(trimethylammonio) ethyl phosphate, 2-methacryloyloxyhexyl-2'-(trimethylammonio) ethyl phosphate, 2-methacryloyloxyethyl-3'-(trimethylammonio) propyl phosphate, 3-methacryloyloxypropyl-3'-(trimethylammonio) propyl phosphate, 4-methacryloyloxybutyl-3'-(trimethylammonio) propyl phosphate, 5-methacryloyloxypentyl-3'-(trimethylammonio) propyl phosphate, 6-methacryloyloxyhexyl-3'-(trimethylammonio) propyl phosphate, 2-methacryloyloxyethyl-4'-(trimethylammonio) butyl phosphate, 3-methacryloyloxypropyl-4'-(trimethylammonio) butyl phosphate, 4-methacryloyloxybutyl-4'-(trimethylammonio) butyl phosphate, 5-methacryloyloxypentyl-4'-(trimethylammonio) butyl phosphate, and 6-methacryloyloxyhexyl-4'-(trimethylammonio) butyl phosphate. MPC is more preferred. It is preferred that the solvent above is 100% ethanol. The ethanol may contain water. It is preferred that the photo-initiator is IRGACURE (D2959), IRGACURE (D369), or benzophenone. IRGACURE (D2959) is most preferred.

Thereafter polymerization is caused by irradiating the substrate with light. A suitable wavelength for the light is 300 nm to 400 nm. The temperature during polymerization is preferably 20° C. to 60° C. and more preferably approximately 60° C. The irradiation time is preferred to be between 10 minutes and 90 minutes and is generally about 10 minutes.

After polymerization, washing is performed by immersion in water or an organic solvent. The organic solvent includes ethanol or acetone and most preferably is ethanol.

Embodiment 2

Figure 2:
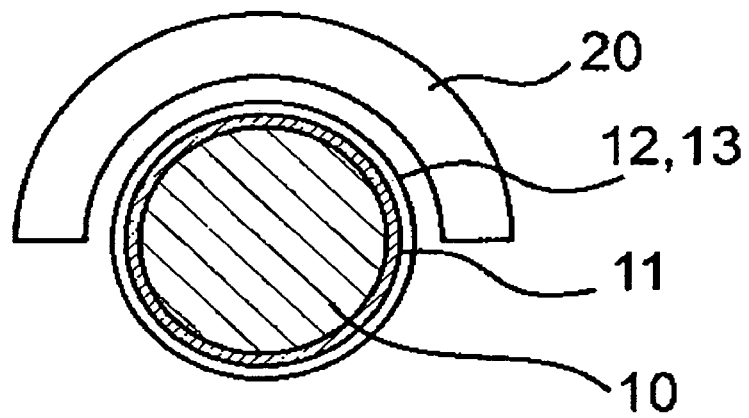
FIG. 2 is a schematic sectional view of a first embodiment of femoral head prosthesis according to the present invention.

FIG. 2 is a cross-sectional view of a joint prosthesis manufactured by the production method of the present invention. As shown in FIG. 2, the joint prosthesis according to the second embodiment of the present invention comprises a femoral head 10 made of metal, alloy or ceramic and an acetabular cup 20 made of organic material. The femoral head 10 has a surface processed layer 11 on at least one section of the femoral head 10. The surface processed layer 11 is formed by processing at least one section of the surface of the femoral head 10. The femoral head 10 has a binder layer 12 laminated on the surface processed layer 11 and a biocompatible material layer 13 laminated on the binder layer 12. The femoral head 10 made of metal, alloy or ceramic in a joint prosthesis according to the second embodiment of the present invention is coated with a biocompatible material layer 13 via the binder layer 12 and the surface processed layer 11 and therefore does not produce wear debris of for example, metal. Moreover even when wear debris is produced from the biocompatible material layer 13 coating the femoral head 10, the wear debris from the biocompatible material layer does not have an adverse effect on the human body. Therefore a joint prosthesis according to the second embodiment can be preferably employed.

Embodiment 3

Figure 3:
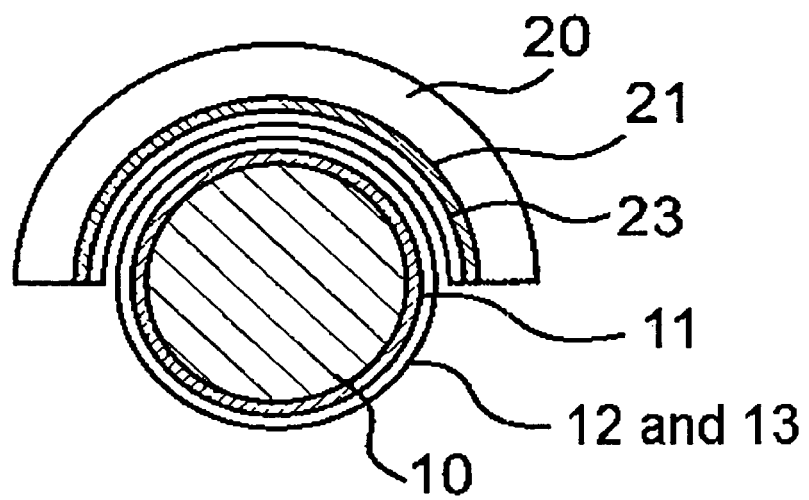
FIG. 3 is a schematic sectional view of a second embodiment of femoral head prosthesis according to the present invention.

As shown in FIG. 3, a joint prosthesis according to the third embodiment of the present invention comprises a femoral head 10 made of metal, alloy or ceramic and an acetabular cup 20 made of organic material. The femoral head 10 and the acetabular cup 20 have a surface-treated layer 11, 21 on at least one section thereof respectively. The surface-treated layer 11 is formed by treatment at least one section of the surface of the femoral head 10 or the acetabular cup 20. The femoral head 10 has a binder layer 12 laminated on the surface-treated layer 11 and a biocompatible material layer 13 laminated on the binder layer 12. These biocompatible material layers 13 are placed in contact.

The acetabular cup 20 is prepared by known methods (disclosed in, for example, Japanese Unexamined Patent Publication (Kokai) No. 2003-310649) in which the acetabular cup 20 is immersed in an acetone solution containing benzophenone, and then is immersed in an aqueous solution containing a biocompatible material after drying, a biocompatible material layer 23 is formed by irradiating with UV radiation at a wavelength of 300 to 400 nm.

In contrast to the joint prosthesis according to the second embodiment, a joint prosthesis according to the third embodiment has a biocompatible material layer 23 formed on the surface of the acetabular cup 20 whereas in the joint prosthesis according to the second embodiment, there is no surface processed layer or the like formed on the surface of the acetabular cup 20. Therefore the third embodiment differs from the second embodiment. The surface of the acetabular cup 20 made of an organic material in the joint prosthesis according to the third embodiment is coated with a biocompatible material layer 23 and wear debris is not produced from the acetabular cup 20 made of organic material, resulting in solving the problem of loosening. Therefore, it can be preferably employed.

Embodiment 4

Figure 4:
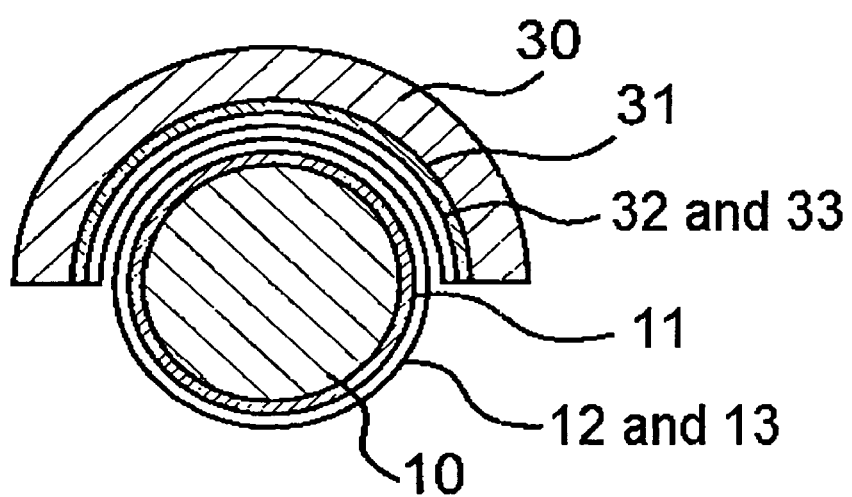
FIG. 4 is a schematic sectional view of a third embodiment of femoral head prosthesis according to the present invention.

As shown in FIG. 4, the joint prosthesis according to the fourth embodiment of the present invention comprises a femoral head 10 made of metal, alloy or ceramic and an acetabular cup 30 made of metal, alloy or ceramic. The femoral head 10 and the acetabular cup 30 have a surface-treated layer 11, 31 on at least one section thereof respectively. The surface-treated layer 11, 31 is formed by treatment at least one section of the surface of the femoral head 10 or the acetabular cup 30. The femoral head 10 and the acetabular cup 30 have a binder layer 12, 32 laminated on the surface-treated layer 11, 31 and a biocompatible material layer 13, 33 laminated on the binder layer 12, 32. These biocompatible material layers 13, 33 are placed in contact.

In the joint prosthesis according to the fourth embodiment, it has an acetabular cup made of metal, alloy or ceramic whereas in the joint prosthesis according to the third embodiment, the acetabular cup is made of organic material and therefore it differs from the joint prosthesis according to the second embodiment. A joint prosthesis according to the fourth embodiment has an acetabular cup made of metal, alloy or ceramic and therefore can be preferably employed due to its superior hardness compared to components made of organic material.

Example 1

Tests were conducted by manufacturing a biomaterial according to the present invention under the conditions below. A Co—Cr—Mo alloy, such as Co-28Cr-6Mo alloy was used as the basic substrate. 4-META was used in the binder layer and MPC as a biocompatible material.

(1) Firstly a sample of the Co—Cr—Mo alloy (composition: Co-28Cr-6Mo) was subjected to ultrasonic cleaning in an acetone solution.

(2) Then the alloy was immersed for 30 minutes in 20 to 45% nitric acid solution and subjected to treatment for increasing the content of Cr (nitric acid treatment).

(3) After the sample is treated with nitric acid solution, it is placed in a plasma etcher and is subjected to oxygen plasma treatment. Thus the surface of the sample was oxidized to a Cr oxide and then transformed into Cr—OH.

(4) The pre-treated surface of the sample is promptly spin-coated with 10% (by weight) 4-META/acetone solution.

(5) Thereafter the sample is dried at 40° C. (in air) for three hours.

(6) Then the sample is immersed into a mixed solution of 0.1% by weight of IRGACURE (D2959) and 2% by weight of MPC/ethanol and is subjected to 350 nm UV irradiation for 10 minutes at 60° C.

(7) After forming an MPC polymer, the sample was let stand overnight in ethanol.

(8) The static wettability of the Co—Cr—Mo alloy sample surface (static water-contact angle) was evaluated using a sessile drop method. The static surface contact angle was measured 60 seconds after dripping pure water in 1 μL droplets.

(9) The condition of surface element of the Co—Cr—Mo sample was analyzed by means of X-ray photoelectron spectroscopy (hereinafter referred to as "XPS"). The analyzation was performed using Mg—Kα rays as X-ray source under the condition of applied voltage 15 kV, take-off angle 90°.

Figure 5:
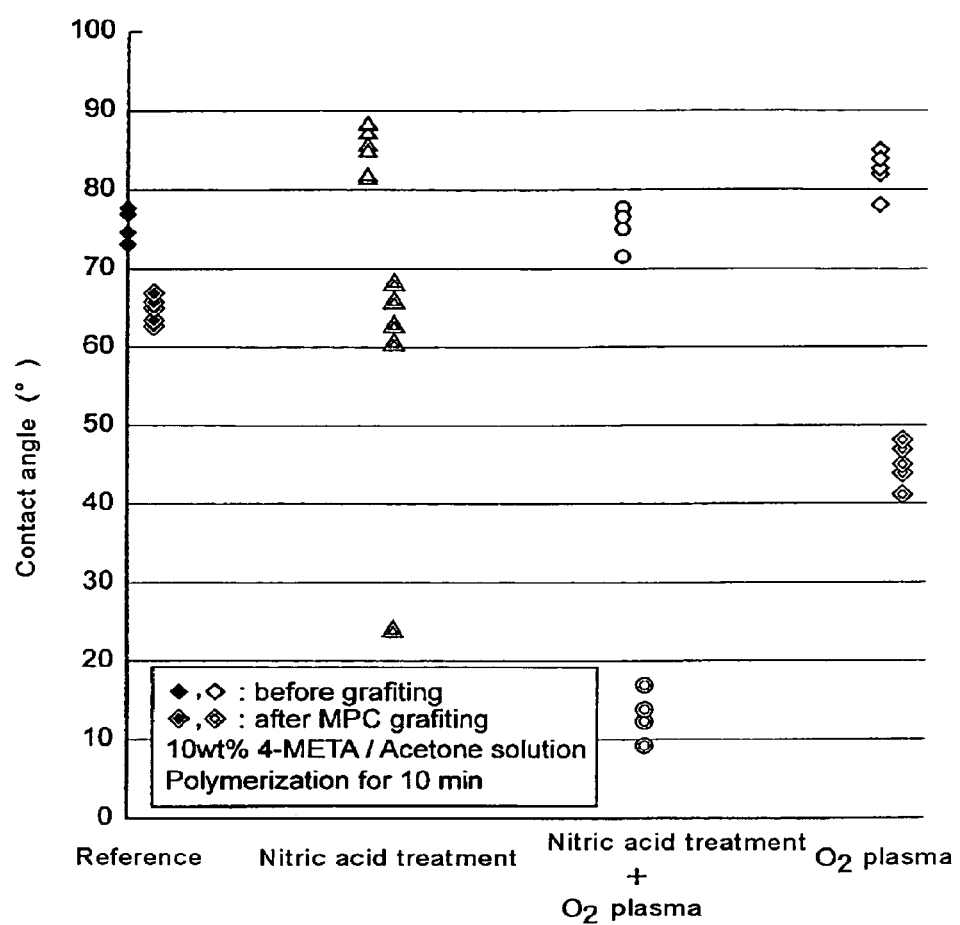
FIG. 5 is a graph comparing the effect of surface treatments.

The measurement results for static surface contact angle are shown in FIG. 5. A static water-contact angle of a Co—Cr—Mo alloy treated with nitric acid treatment and then oxygen plasma treatment has an extremely low value of 10 to 20°. The contact angle of a MPC-coated femoral head made of Co—Cr—Mo alloy which is treated with either of nitric acid treatment or oxygen plasma treatment prior to 4-META coating was measured to be merely 40 to 70°.

The results of XPS analysis are shown in Table 1. The concentration of nitrogen and phosphorus atoms originating from MPC in MPC-coated Co—Cr—Mo alloy treated with both of nitric acid treatment and subsequent oxygen plasma treatment are high values of 2.5 and 2.1 respectively. However the concentration of nitrogen and phosphorus atoms in the sample of MPC-coated Co—Cr—Mo alloy treated with either of nitric acid treatment or oxygen plasma treatment prior to 4-META coating displayed a low effect of 0.6 to 1.0, and 0.7 to 2.0 respectively.

TABLE 1

| MPC coating | Pre-Treatment | Atom concentration (atom %) | |
|---|---|---|---|
| | | $N_{1S}$ | $P_{2P}$ |
| Without MPC coating | No pre-treatment | 0.5 | 0.0 |
| | Nitric acid treatment + $O_2$ plasma treatment | 0.0 | 0.0 |
| With MPC coating | No pre-treatment | 0.6 | 0.7 |
| | Nitric acid treatment | 1.0 | 2.0 |
| | Nitric acid treatment + $O_2$ plasma treatment | 2.5 | 2.1 |

Example 2

Tests were conducted by manufacturing a biomaterial according to the present invention under the conditions below. The composition used as the substrate was a Ti—Al—V alloy, for example, Ti-6Al-4V. 4-META was used in the binder layer and MPC as a biocompatible material.

(1) Firstly a sample of the Ti alloy (composition: Ti-6Al-4V) was subjected to ultrasonic cleaning in an acetone solution.

(2) The sample was placed in a plasma treatment device and subjected to oxygen plasma treatment. Therefore, titanium oxides are formed on the Ti alloy surface to be transformed into Ti—OH.

(3) The pre-treated surface of the sample is promptly spin-coated with 10% 4-META/acetone.

(4) Thereafter the sample is dried at 40° C. (in air) for three hours.

(5) Then the femoral head is immersed in a mixed solution of 0.1% by weight of IRGACURE (D2959) and 2% by weight of MPC monomer/ethanol and irradiated for 10 minutes at 60° C. using UV radiation at 350 nm.

(6) After forming the MPC polymer, the sample was let stand overnight in ethanol.

(7) The test sample was prepared using a Ti-6Al-4V which was spin-coated with MPC-butylmethacrylate copolymer.

(8) The static wettability of the Ti-6Al-4V alloy sample surface (static water-contact angle) was evaluated using a sessile drop method. The static water-contact angle was measured at 60 seconds after dripping pure water in 1 μL droplets. The results are shown. The surface contact angle of the Ti-6Al-4V alloy coated by MPC polymer in which an MPC monomer is graft-polymerized on the alloy has an extremely low value of 10 to 20°. The contact angle of a MPC-butylmethacrylate copolymer spin-coated Ti-6Al-4V alloy was 70 to 80° and showed almost no effect.

Example 3

Tests were conducted by manufacturing a biomaterial according to the present invention under the conditions below. The composition used as the substrate was a Co—Cr—Mo alloy having the following constitution: Co-28Cr-6Mo. 4-META was used in the binder layer and MPC as a biocompatible material.

1. Processing of Femoral Head Ball

A femoral head ball made of a Co—Cr—Mo alloy was prepared as described below in (a), (b) or (c).

(a) Co—Cr—Mo alloy (composition: Co-28Cr-6Mo) was cut from a rod, the external shape was processed into a ball and the surface mirror finished.

(b) Co—Cr—Mo alloy (composition: Co-28Cr-6Mo) was cast into a ball shape and the surface mirror finished.

(c) A rod of Co—Cr—Mo alloy (composition: Co-28Cr-6Mo) was cast, the external shape was processed into a ball and the surface mirror finished.

2. Pre-Treatment (1) A femoral head ball made of Co—Cr—Mo alloy was subjected to ultrasonic cleaning in an acetone solution.

(2) The alloy was immersed in 20 to 45% nitric acid solution for 30 minutes and subjected to treatment for increasing the content of Cr (nitric acid treatment).

(3) The nitric-acid treated femoral head ball was placed in a plasma treatment device and the surface of the femoral head was oxidized to a Cr oxide and then transformed into Cr—OH.

(4) The pre-treated surface of the femoral head ball was promptly spin-coated with 10% 4-META/acetone and thereafter dried at 40° C. (under normal pressure) for three hours.

3. MPC Treatment (1) The pre-treated femoral head is immersed in a mixed solution of 0.1% by weight of IRGACURE (D2959) and 2% by weight of MPC/ethanol and irradiated for 10 minutes at 60° C. using UV irradiation at 350 nm.

(2) After forming an MPC polymer, the sample was let stand overnight in ethanol.

The invention claimed is:

1. A method for producing a biomaterial having a substrate made of a metal, an alloy or a ceramic material and a biocompatible material layer laminated at appropriate positions on the substrate, comprising the steps of:
   (a) plasma-treating the substrate made of a metal, an alloy or a ceramic material containing a metal component or a metal oxide capable of forming hydroxyl groups to form hydroxyl groups on the surface of the substrate;
   (b) applying a solution containing a binder constituent to the substrate and then drying the solution to form a binder layer thereon, the binder constituent being an organic compound having carboxyl groups on one terminal and methacrylic groups or methylene groups on the other terminal; and
   (c) immersing the substrate in a solution containing a biocompatible material and a photo-initiator and then polymerizing the biocompatible material monomer on the binder layer by UV irradiation to graft-coat the biocompatible material layer on the binder layer.

2. The method for producing a biomaterial according to claim 1, wherein the substrate is made of at least one selected from the group consisting of cobalt-chromium alloy, cobalt-chromium-molybdenum alloy, nickel-chromium alloy, and stainless steel alloy, and the step (a) further comprises a pre-treatment in which a surface of the alloy substrate is treated with nitric acid to increase a concentration of chromium on the surface of the substrate.

3. The method for producing a biomaterial according to claim 2, wherein the binder is made of at least one selected from the group consisting of 4-methacryloxyethyltrimellitate anhydride and 4-methacryloyloxy ethyl trimellitic acid, while the biocompatible material is made of a polymer containing phosphorylcholine groups,
   and the biocompatible material layer is laminated on the substrate by the binder.

4. The method for producing a biomaterial according to claim 2, wherein the binder layer is made of at least one selected from the group consisting of 4-methacryloxyethyltrimellitate anhydride, 4-methacryloyloxy ethyl trimellitic acid and methacrylic acid, while the biocompatible material layer is made of 2-methacryloyloxyethyl phosphorylcholine,
   the methacrylic groups in 4-methacryloxyethyltrimellitate anhydride, 4-methacryloyloxy ethyl trimellitic acid or methacrylic acid react with the methacrylic groups in 2-methacryloyloxyethyl phosphorylcholine into the formation of covalent bonds,
   and the biocompatible material layer is laminated on the substrate by carboxyl groups in the binder layer.

5. The method for producing a biomaterial according to claim 2, wherein the binder layer is made of at least one selected from the group consisting of maleic anhydride and maleic acid, while the biocompatible material layer is made of 2-methacryloyloxyethyl phosphorylcholine,
   methacrylic groups in the 2-methacryloyloxyethyl phosphorylcholine monomer are combined with radicals as nucleus for the graft-polymerization, the radicals being produced by cleaving C—H bond in the maleic anhydride or maleic acid,
   the biocompatible material layer is laminated on the substrate by carboxyl groups in the binder layer.

* * * * *